United States Patent
Morgan (10) Patent No.: US 9,050,053 B2
(45) Date of Patent: Jun. 9, 2015

(54) ULTRASOUND DEVICE WITH CAVITY FOR CONDUCTIVE MEDIUM

(71) Applicant: G. Chad Morgan, Chattanooga, TN (US)

(72) Inventor: G. Chad Morgan, Chattanooga, TN (US)

(73) Assignee: Naimco, Inc., Chattanooga, TN (US)

( * ) Notice: Subject to any disclaimer, the term of this patent is extended or adjusted under 35 U.S.C. 154(b) by 0 days.

(21) Appl. No.: 14/096,641

(22) Filed: Dec. 4, 2013

(65) Prior Publication Data

US 2014/0236016 A1 Aug. 21, 2014

Related U.S. Application Data

(60) Provisional application No. 61/765,361, filed on Feb. 15, 2013, provisional application No. 61/792,909, filed on Mar. 15, 2013.

(51) Int. Cl.
*A61B 8/14* (2006.01)
*A61B 8/00* (2006.01)

(52) U.S. Cl.
CPC .............. *A61B 8/4444* (2013.01); *A61B 8/4281* (2013.01); *A61B 8/4483* (2013.01)

(58) Field of Classification Search
None
See application file for complete search history.

(56) References Cited

U.S. PATENT DOCUMENTS

| | | | |
|---|---|---|---|
| 4,383,529 A | 5/1983 | Webster | |
| 4,787,888 A | 11/1988 | Fox | |
| 5,078,149 A | 1/1992 | Katsumata et al. | |
| 5,212,988 A | 5/1993 | White et al. | |
| 5,415,629 A | 5/1995 | Henley | |
| 5,460,595 A | 10/1995 | Hall et al. | |
| 5,494,038 A | 2/1996 | Wang et al. | |
| 5,558,623 A * | 9/1996 | Cody | 601/2 |
| 5,575,291 A * | 11/1996 | Hayakawa et al. | 600/459 |
| 5,626,554 A | 5/1997 | Ryaby et al. | |
| 5,628,730 A | 5/1997 | Shapland et al. | |
| 5,655,539 A | 8/1997 | Wang et al. | |
| 5,770,801 A * | 6/1998 | Wang et al. | 73/644 |
| 5,997,481 A | 12/1999 | Adams et al. | |
| 6,132,378 A | 10/2000 | Marino | |
| 6,176,842 B1 | 1/2001 | Tachibana et al. | |
| 6,477,410 B1 | 11/2002 | Henley et al. | |
| 6,599,246 B1 | 7/2003 | Coffey et al. | |
| 6,720,402 B2 | 4/2004 | Langer et al. | |
| 6,937,893 B2 | 8/2005 | Danz et al. | |

(Continued)

FOREIGN PATENT DOCUMENTS

| | | |
|---|---|---|
| EP | 0527651 A1 | 2/1993 |
| JP | 3063071 | 3/1991 |

(Continued)

OTHER PUBLICATIONS

English translation of WO 2009/109196.*

(Continued)

*Primary Examiner* — Long V Le
*Assistant Examiner* — Bradley Impink
(74) *Attorney, Agent, or Firm* — Kraguljac Law Group, LLC (57) ABSTRACT

Devices and systems are disclosed that are associated with ultrasound sound devices. In one embodiment, a diaphragm for an ultrasound device comprises a housing configured with a receiving cavity defined by one or more sidewalls, wherein the receiving cavity is configured to hold a conductive medium. A connector formed in the housing is configured to connect the diaphragm to an ultrasound device.

22 Claims, 8 Drawing Sheets

(56) References Cited

U.S. PATENT DOCUMENTS

| | | |
|---|---|---|
| 7,283,874 B2 | 10/2007 | Penner |
| 8,226,562 B2 | 7/2012 | Pelissier et al. |
| 8,672,851 B1 * | 3/2014 | Quirk et al. ............... 600/459 |
| 2002/0156415 A1 | 10/2002 | Redding |
| 2005/0096547 A1 | 5/2005 | Wendelken et al. |
| 2005/0165393 A1 | 7/2005 | Eppstein |
| 2005/0215901 A1 | 9/2005 | Anderson et al. |
| 2005/0283110 A1 * | 12/2005 | Atala et al. ............... 604/20 |
| 2006/0015058 A1 | 1/2006 | Kellogg et al. |
| 2006/0184070 A1 | 8/2006 | Hansmann et al. |
| 2006/0264751 A1 | 11/2006 | Wendelken et al. |
| 2007/0299369 A1 * | 12/2007 | Babaev ............... 601/2 |
| 2008/0033292 A1 | 2/2008 | Shafran |
| 2008/0139944 A1 | 6/2008 | Weymer et al. |
| 2008/0140026 A1 | 6/2008 | Sliwa et al. |
| 2008/0195003 A1 | 8/2008 | Sliwa et al. |
| 2008/0200810 A1 | 8/2008 | Buchalter |
| 2009/0043205 A1 * | 2/2009 | Pelissier et al. ............... 600/446 |
| 2009/0112133 A1 | 4/2009 | Deisseroth et al. |
| 2009/0318813 A1 * | 12/2009 | Thompson et al. ............... 600/459 |
| 2010/0022889 A1 * | 1/2010 | Caberg et al. ............... 600/459 |
| 2010/0132450 A1 | 6/2010 | Pomerantz et al. |
| 2010/0152644 A1 | 6/2010 | Pesach et al. |
| 2011/0077555 A1 | 3/2011 | Wing et al. |
| 2012/0277640 A1 | 11/2012 | Lewis, Jr. et al. |
| 2013/0006153 A1 | 1/2013 | Lewis, Jr. |
| 2013/0144193 A1 | 6/2013 | Lewis, Jr. et al. |

FOREIGN PATENT DOCUMENTS

| | | |
|---|---|---|
| WO | 9942528 A2 | 8/1999 |
| WO | 0207590 A2 | 1/2002 |
| WO | WO 2009109196 A1 * | 9/2009 |
| WO | 2011082402 A2 | 7/2011 |

OTHER PUBLICATIONS

English translation of KR 10-2012-0113105.*
Patent Cooperation Treaty (PCT) International Search Report and Written Opinion in co-pending PCT International Appl. No. PCT/US2013/073308 (International Filing Date Dec. 5, 2013) having a date of mailing of Feb. 26, 2014 (14 pgs.).
U.S. Appl. No. 09/625,339, filed Jul. 25, 2000, Menezes
Patent Cooperation Treaty (PCT) International Search Report and Written Opinion in PCT International Appl. No. PCT/US2014/028202 (International Filing Date of Mar. 14, 2014) having a date of mailing of Aug. 7, 2014 (9 pgs.).
Patent Cooperation Treaty (PCT) International Search Report and Written Opinion in PCT International Appl. No. PCT/US14/16515 (International Filing Date of Feb. 14, 2014) having a date of mailing of Apr. 29, 2014 (11 pgs.).
Patent Cooperation Treaty (PCT) International Search Report and Written Opinion in PCT International Appl. No. PCT/US2014/016481 (International Filing Date of Feb. 14, 2014) having a date of mailing of May 13, 2014 (9 pgs.).

* cited by examiner

ULTRASOUND DEVICE WITH CAVITY FOR CONDUCTIVE MEDIUM

CROSS REFERENCE TO RELATED APPLICATIONS

This disclosure claims the benefit of U.S. Provisional Patent Application with Ser. No. 61/765,361 filed on Feb. 15, 2013, entitled "Ultrasound device with recessed diaphram," and U.S. Provisional Patent Application with Ser. No. 61/792,909, filed Mar. 15, 2013, entitled "Alternating frequency ultrasound device," which are both hereby incorporated by reference in their entirety.

BACKGROUND

Ultrasound devices operate with frequencies from 0 to 200 mHz up to several gigahertz and are used in many different fields. In the medical field, ultrasound can be used for therapeutic procedures and imaging of internal structures. For example, ultrasound can be applied to a patient's skin to stimulate the tissue beneath the skin's surface using very high frequency sound waves.

Ultrasound is applied using a device that includes a transducer or applicator that is put in contact with a patient's skin. Gel is dispensed on the patient's skin to cover the area and on all surfaces of the device's head to couple the device with the skin, to reduce friction, and to assist transmission of the ultrasonic waves. The gel is squeezed out of a bottle and spread over the patient's skin. Since the gel is a fluid, it is difficult to contain within a desired area of the skin and the thickness of the gel cannot be controlled. Lack of a consistent and desired thickness of the gel can lead to a less than optimal ultrasound application. Gel that is too thin or too thick can affect the quality of images produced by the device, therapeutic values, and/or efficacy. Furthermore, when the ultrasound procedure is completed, the patient is required to clean up and wipe off the gel from the patient's skin. Typically, the gel is not completely removed and the cleaning process is uncomfortable.

SUMMARY

In one aspect of the disclosure, a diaphragm for an ultrasound device comprises a housing configured with a receiving cavity defined by one or more sidewalls, wherein the receiving cavity is configured to hold a conductive medium. A connector is formed in the housing for connecting the diaphragm to an ultrasound device.

In another aspect of the disclosure, a head assembly for an ultrasound device is disclosed that comprises a housing configured with a diaphragm wall disposed within the housing; a sidewall formed around a perimeter of the diaphragm wall and extending out from the diaphragm to define a first cavity, wherein the first cavity is configured to receive a portion of a conductive medium; a second cavity in the housing for containing an ultrasound transducer for generating ultrasound energy, wherein the ultrasound transducer is connected to an internal surface of the diaphragm wall; and a connector formed in the housing for connecting the head assembly to an ultrasound device.

In another aspect of the disclosure, an ultrasound device comprises a housing configured with a handle portion and a head portion; one or more sidewalls extending out from the head portion that defines a receptacle configured to hold a portion of conductive medium; and a transducer connected within the head portion and configured to generate ultrasound energy to be transmitted through the receptacle.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, or other shapes) in the figures represent one embodiment of the boundaries. In some embodiments one element may be designed as multiple elements or that multiple elements may be designed as one element. In some embodiments, an element shown as an internal component of another element may be implemented as an external component and vice versa. Furthermore, elements may not be drawn to scale.

DETAILED DESCRIPTION

Various embodiments of an ultrasound device are disclosed herein that are configured to operate with a controlled or predefined amount of gel (or other conductive medium) used during an ultrasound procedure. In one embodiment, an ultrasound device is described herein that includes a diaphragm configured with a recessed cavity/receptacle for containing a conductive medium. The diaphragm is also referred to herein as a head assembly since the diaphragm is part of the head of an ultrasound device. In another embodiment, a diaphragm is disclosed that is configured as a replaceable head for an ultrasound or other imaging technology device where the diaphragm includes an ultrasound transducer or other imaging technology transducer (e.g., piezoelectric crystal) and a cavity for containing a conductive medium.

Figure 1A:
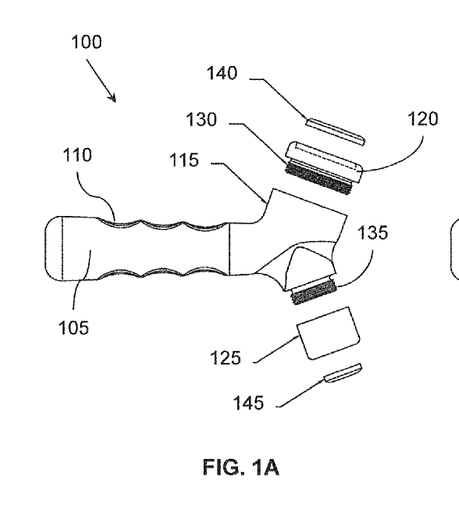
FIG. 1A illustrates one embodiment of an ultrasound device shown with a head assembly that is detached.
Figure 1B:
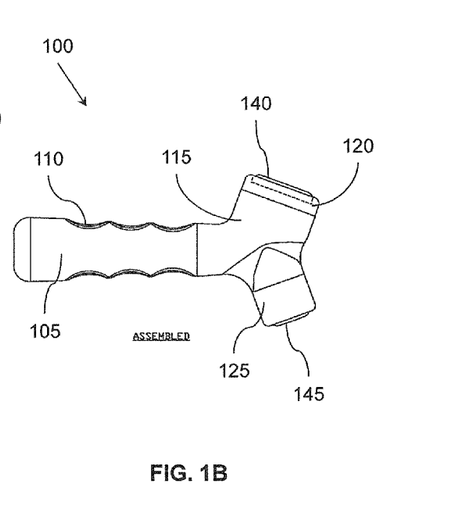
FIG. 1B illustrates the ultrasound device of FIG. 1A with the head assembly attached.

With reference to FIG. 1A and FIG. 1B, one embodiment of an ultrasound device 100 is shown in a partially unassembled state (FIG. 1A) and in an assembled state (FIG. 1B).

The device 100 is configured as a hand-held device/probe including an elongated handle 105 that may include zero or more finger grips 110 (e.g., indentations, ridges, and so on). The handle 105 is connected to a head 115 that includes one or more sides that connect to a diaphragm. In the illustrated embodiment, the head 115 includes two sides where the first side includes diaphragm 120 and the second side includes diaphragm 125.

In general as discussed herein, the diaphragm 120, 125 is the component that is formed or connected as part of the head (sometimes referred to as the nose) of an ultrasound device/ probe. The diaphragm may also be an acoustic member or acoustic lens such that ultrasound energy generated from a transducer is directed and transmitted through the acoustic lens/diaphragm, and in imaging probes, echo signals are received from a subject through the acoustic lens/diaphragm.

In one embodiment, diaphragm 120 is configured with a connector 130 that is threaded to insert and connect with a corresponding threaded socket in the head 115. Similarly, the second side of the head 115 may include a connector 135 that is threaded for connecting with a threaded socket within the diaphragm 125. In another embodiment, the connectors 130 and 135 may be configured as a quick-connect/disconnect device so that the diaphragms 120 and 125 can be connected by pushing and snapping into place or disconnected by pulling off with a small amount of force. In another embodiment, the diaphragm 120 may be configured to slide on/off and connect by friction. Thus, in one embodiment, the diaphragms 120 or 125 are configured as replaceable components that can be removed and attached to other devices (e.g., attachable and detachable). Being replaceable allows for different sized diaphragms to be connected to the head 115 so that the same device 100 can be configurable with different sized diaphragms and different sized transducers that may be attached within the diaphragm. In another embodiment, the head 115 and diaphragm 125 may be integral with each other (see example in FIG. 5).

Figures 2A, 2B:
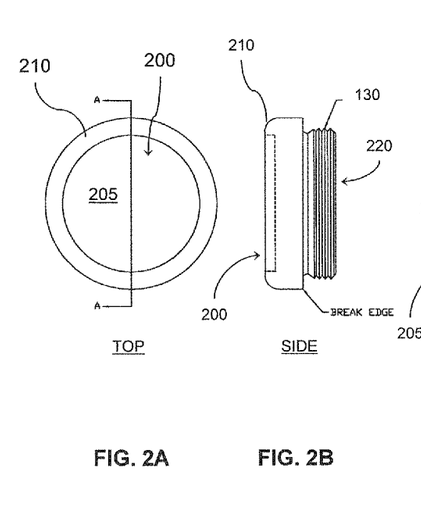
FIGS. 2A-2D illustrate various views of one embodiment of a diaphragm.

With reference to diaphragm 120, the diaphragm includes a recessed cavity/receptacle that is configured to receive and contain/hold a conductive medium 140 used during an ultrasound or imaging scan. The cavity is configured to allow the conductive medium to be inserted into and removed from the cavity. In one embodiment, the conductive medium 140 is a portion of gel (e.g., preconfigured gel, gel pad) that is manufactured to maintain its dimensions (e.g., may be elastic with memory, flexible, and/or semi-solid or solid, etc.). The preconfigured medium 140 fits into the cavity, as seen in FIG. 1B where the medium 140 is inserted into the cavity of diaphragm 120. Likewise, diaphragm 125 includes a cavity to receive a conductive medium 145 when used during a scan. The diaphragm 120 is explained in more detail with reference to FIG. 2.

Figures 2C, 2D:
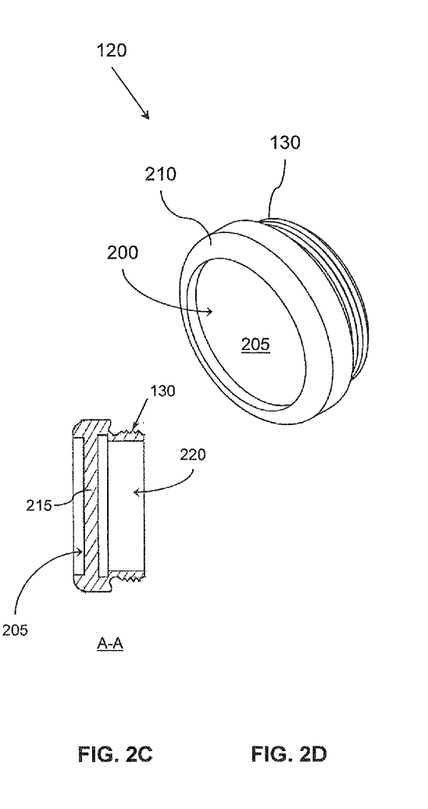

With reference to FIGS. 2A-2D, one embodiment of diaphragm 120 (e.g., head assembly) is shown in a Top View FIG. 2A, Side View FIG. 2B, Cross-Section View FIG. 2C through A-A of FIG. 2A, and a Perspective View FIG. 2D.

In one embodiment, the diaphragm 120 includes a housing formed from metal, metallic, or other conductive material that functions with ultrasound energy (e.g., plastic or other acoustic conducting material). The diaphragm 120 includes a cavity/receptacle 200 that is configured to receive a conductive medium. For example, the cavity 200 is a gel receiving cavity (e.g., a receptacle in which gel is inserted for an ultrasound procedure). The cavity 200 is defined by diaphragm surface 205 and a sidewall 210 that extends out from the diaphragm surface 205. The diaphragm surface 205 is the outer surface of a wall or partition 215 that forms the diaphragm and extends across the interior of the housing as seen in FIG. 2C. Stated another way, the diaphragm surface 205 is recessed within the housing from the top of the sidewall 210 to define the cavity 200 for receiving gel.

Thus in one embodiment, the recessed diaphragm wall 215 defines two cavities within the housing of the diaphragm 120, namely, cavity 200 and cavity 220. The diaphragm surface 205 is shown as generally a circular shape but other shapes may be used (e.g., oval, rectangular, area with curved edges, flat or arced surface, polygon, and so on). In one embodiment, the diaphragm surface 205 is substantially flat but may be arced depending on the desired shape of the diaphragm 120. In another embodiment, the diaphragm wall 215 does not extend across the entire area of the housing but may extend a portion out from the side wall 210 such that the wall 215 has an opening therethrough.

Connector 130 may be threaded on either the outside or inside surface of the housing. In another embodiment, the connector 130 may be configured as a snap-on/snap-off connector (e.g., quick connect coupling) to attach to the head of an ultrasound device/probe. Other attachment mechanisms may be used (e.g., friction fit, adhesion, and so on).

In one embodiment, the sidewall 210 is a continuous edge or rim around the perimeter of the diaphragm surface 205. In another embodiment, the sidewall 210 may include one or more notches (not shown). A notch may be used to assist with removing gel from within the cavity 200 by inserting a finger in the notch to access the gel within the cavity from the side and lift out the gel. In another embodiment, the sidewall 210 may be perforated or be configured as two or more portions such as prongs that can hold a piece of solid gel (e.g., gel 140 shown in FIGS. 1A and 1B).

The cavity 205 is configured as a containment area for receiving a conductive medium (e.g., a gel shot, preconfigured piece of semi-solid gel). In one embodiment, the conductive medium is configured to correspond to fit into the shape of the cavity 205. A piece of gel can be inserted into the cavity 200 where the gel is held in place by at least surface tension with the surface 205 and/or friction with the inside surface of the sidewall 210. In this manner, the diaphragm 120 self-contains the gel to be used during an ultrasound scan/ procedure so that the gel moves with the ultrasound device as the device is moved over a subject. Thus the diaphragm 120 maintains the position of the gel piece relative to the transducer within the ultrasound device during movement of the ultrasound device. The cavity 200 and sidewall 210 form a mechanism for holding and moving a piece of gel during a scan. When the scan is complete, the gel is simply removed from the cavity 200 and another piece of gel can be inserted for a subsequent scan (see FIGS. 4A and 4B that show an example piece of gel 140 being inserted into the cavity 200).

As such, the amount of gel used during a scan is fully controlled by the piece of preconfigured gel. Furthermore, the preconfigured gel provides for greater sterility because pieces of gel can be packaged individually to prevent contamination. Dispensing and applying liquid gel on a patient in a random and immeasurable manner is eliminated. Furthermore, using a controlled amount of gel reduces the amount of gel needed for a scan, which can reduce the cost of using gel.

FIG. 2C illustrates a cross-section view of the diaphragm 120 through A-A of FIG. 2A and side view of FIG. 2B. The various dimensions shown are only exemplary of one embodiment. It is not intended to limit the construction of the diaphragm 120 shown since the diaphragm can be formed with different shapes and sizes.

Figure 3:
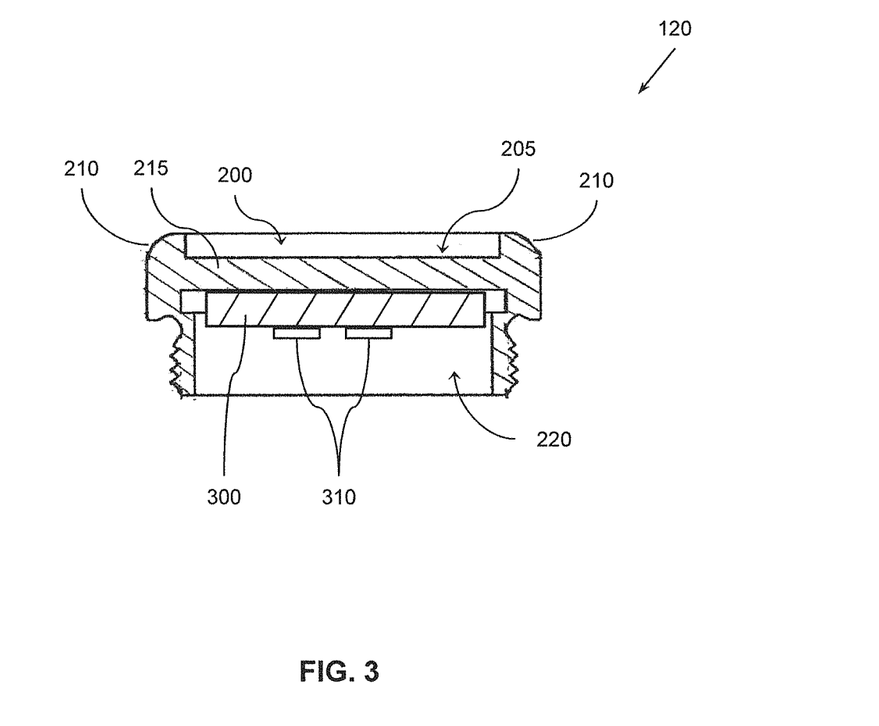
FIG. 3 illustrates a cross-section view of FIG. 2C including one embodiment of an ultrasound transducer disposed within the diaphragm.

With reference to FIG. 3, another embodiment of the cross-section view of FIG. 2C is shown. In FIG. 3, a transducer 300 is positioned and attached within the interior cavity 220. For example, the transducer 300 may be attached by an adhesive to the inside surface of the diaphragm wall 215, attached by friction, or attached by contact with other assembled components that hold the transducer 300 in place. In one embodiment, the transducer 300 is positioned adjacent the gel receiving cavity 200 on the opposite side of the diaphragm wall 215 such that ultrasound energy generated by the transducer 300 is directed towards and transmitted through the diaphragm wall 215 and the gel receiving cavity 200.

In one embodiment, the transducer 300 may include one or more electrical contacts 310 (e.g., pins, tabs, electrodes, wire connectors, and so on) to electrically connect the transducer 300 to a driving circuit and/or power supply when the diaphragm 120 is connected to an ultrasound device. In one embodiment, the transducer is a piezoelectric crystal for generating ultrasound waves.

Figure 4A:
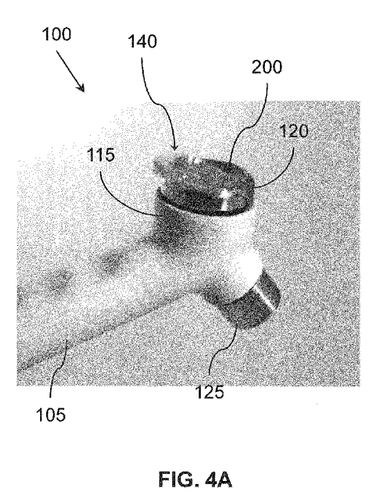
FIG. 4A shows gel being inserted into a cavity of an ultrasound device/probe.
Figure 4B:
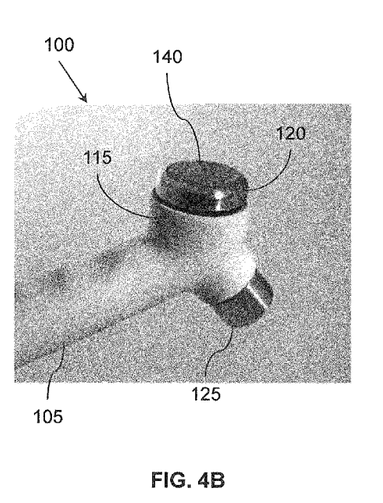
FIG. 4B shows the gel in an inserted state in the cavity of the ultrasound device/probe.

With reference to FIG. 4A, in another embodiment, the piece of preconfigured gel 140 is shown being inserted into the cavity 200 of the diaphragm 120 (or head 115). FIG. 4B shows the gel 140 in an inserted state in the cavity 200. As seen in FIG. 4B, the cavity 200 is configured to contain/enclose multiple sides of the preconfigured gel 140 while at least one side of the preconfigured gel 140 is exposed (e.g., top surface). The exposed surface is the surface that is placed in contact with the skin of a patient (or other object) to which ultrasound is applied.

In one embodiment, the diaphragm 120 is configured to convert the head portion 115 of the ultrasound device from an existing configuration that does not have a gel receiving cavity to a configuration that includes the gel receiving cavity 200 after the diaphragm 120 is connected to the ultrasound device. This may involve removing an existing head assembly and replacing it with the diaphragm 120 or (depending on the configuration), attaching the diaphragm 120 on top of an existing head assembly. Thus an existing ultrasound device can be retrofitted to include the gel receiving cavity 200.

Figure 5:
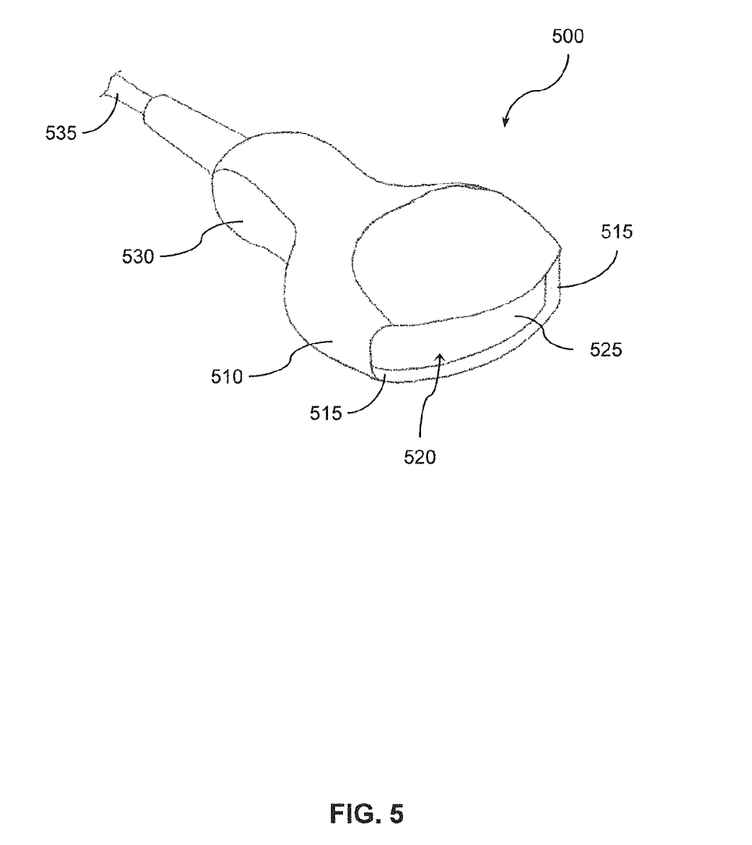
FIG. 5 illustrates another embodiment of an example ultrasound probe with a gel cavity configured in the housing.

With reference to FIG. 5, another embodiment of a handheld ultrasound probe/device 500 is shown that is configured with an integrated head assembly. For example, instead of the device having a detachable diaphragm 120 as in the embodiment of FIG. 1A, the ultrasound device 500 includes a housing that has a head portion 510 that is integrated with and forms side wall 515. The side wall 515 defines a gel receiving cavity 520 similar to the cavity 200 in FIG. 2D.

The side wall 515 extends around an acoustic member or acoustic lens 525 through which ultrasound energy is transmitted from a transducer (not shown). The transducer is positioned within the housing behind the acoustic lens 525. With the gel receiving cavity 520, a piece of preconfigured gel may be inserted and contained within the cavity 520. The cavity 520 is configured to hold the preconfigured gel against the acoustic lens 525 and move the gel along a patient as the ultrasound device 500 is moved. Thus the device 500 and the gel are moved together. Other components may include a handle portion 530 and a power supply cord 535 or may have an internal power source.

With the gel receiving cavity 520, preconfigured gel is used that has a predefined/measured amount of gel. Thus the gel provides a known thickness and a consistent amount of gel during an ultrasound procedure. In this manner, the device 500 (or device 100 from FIG. 1A) is configured to provide and use a controlled amount of gel during a procedure, which eliminates the random dispensing of liquid gel on a patient.

Figure 6:
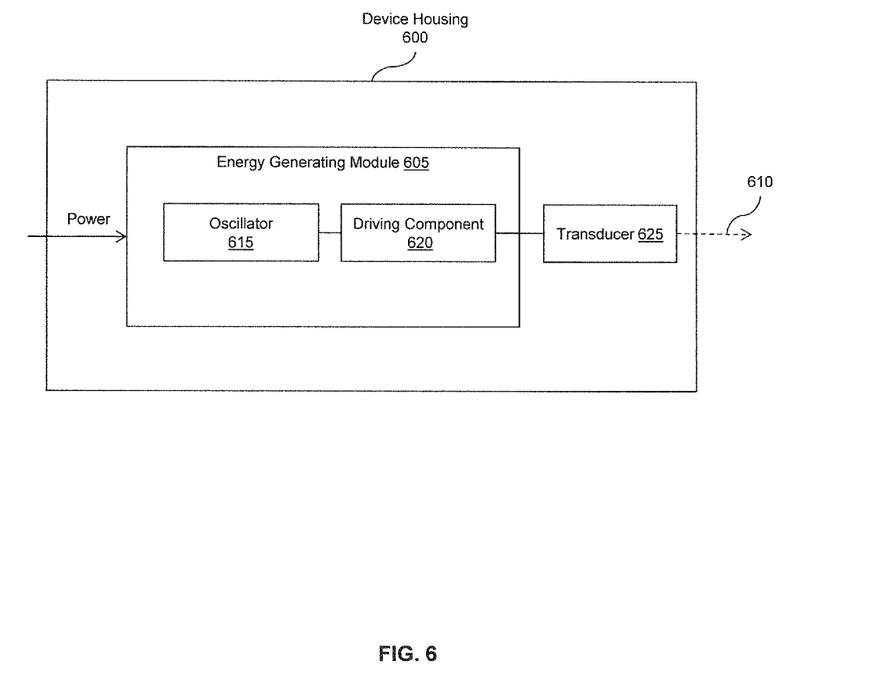
FIG. 6 illustrates one embodiment of a block diagram of an ultrasound device with energy generating components.

With reference to FIG. 6, one embodiment of the components within a housing 600 that may be the housing of the ultrasound device 100 or 500 is shown. The components are configured to generate and/or detect ultrasound energy. In one embodiment, the housing 600 includes an energy generating module 605 operative to generate a driving signal that can be transformed into ultrasonic energy 610. The energy generating module 605 can be implemented as a circuit board with electrical components that are electrically connected, in one embodiment. The energy generating module 605 includes a local power source or receives power from a remote source via a power cord, an oscillator 615, and a driver component 620. There are many different types and combinations of internal components that can be used to implement the ultrasound device. Since they are not the focus of the present disclosure, they are not described in detail.

In one embodiment, the housing 600 also includes an ultrasound transducer 625 having a piezoelectric component. The ultrasound transducer 625 is operative to receive the driving signal from the energy generating module 605 and transform the driving signal into ultrasonic energy 610. If the ultrasound device is an imaging device, the housing 600 may contain components to detect, store, and convert received ultrasound signals. In another embodiment, the ultrasound transducer 625 is part of the head assembly as previously described (e.g., see FIG. 3).

In one embodiment, the transducer 625 is a piezoelectric transducer that converts electrical energy into sound. Piezoelectric crystals have the property of changing size when a voltage is applied, thus applying an alternating current (AC) across the crystal causes the crystal to oscillate at very high frequencies, thus producing very high frequency sound waves.

The location at which a transducer focuses the sound can be determined by the active transducer area and shape, the ultrasound frequency, and the sound velocity of the propagation medium.

Since piezoelectric crystals generate a voltage when force is applied to them, the same crystal can be used as an ultrasonic detector/receiver. In other embodiments, separate transmitter and receiver components may be implemented.

In another embodiment, a non-piezoelectric transducer may be implemented. For example, the transducer 625 may be constructed of magnetostrictive materials that change size when exposed to a magnetic field.

In another embodiment, the housing 600 may include an internal memory for storing ultrasound data collected by the device. The housing 600 may include an interface for communicating the data from the memory to a remote device. The ultrasound device 600 can be configured to communicate the data via a wire connection and/or a wireless connection to a host machine or computer.

Alternating Frequency Embodiment

Therapeutic ultrasound treatment is customarily performed manually by a clinician. The clinician applies and moves a handheld ultrasound device over an area of a patient. The area being treated on the patient is typically larger than the size of the head/tip of the ultrasound device. Thus the clinician must carefully move the ultrasound device across a patient's skin with a coupling/conductive medium (e.g., layer of gel or lotion) between the transducer and the skin. The movement is also needed to avoid damaging the skin caused by "hot spots" from the ultrasound device. For example, if the device is left in one location for too long, the continuous ultrasound energy can overexpose and burn the skin. This may happen in a few seconds depending on the intensity of the ultrasound.

Movement speed of the transducer during treatment varies widely from one clinician to another. Therefore, many clinicians incorrectly apply the ultrasound by moving the transducer too fast, by not using enough coupling medium, by not moving the transducer, by trying to treat too large of an area, by not keeping the transducer in contact with the patient or other faults.

Figure 7:
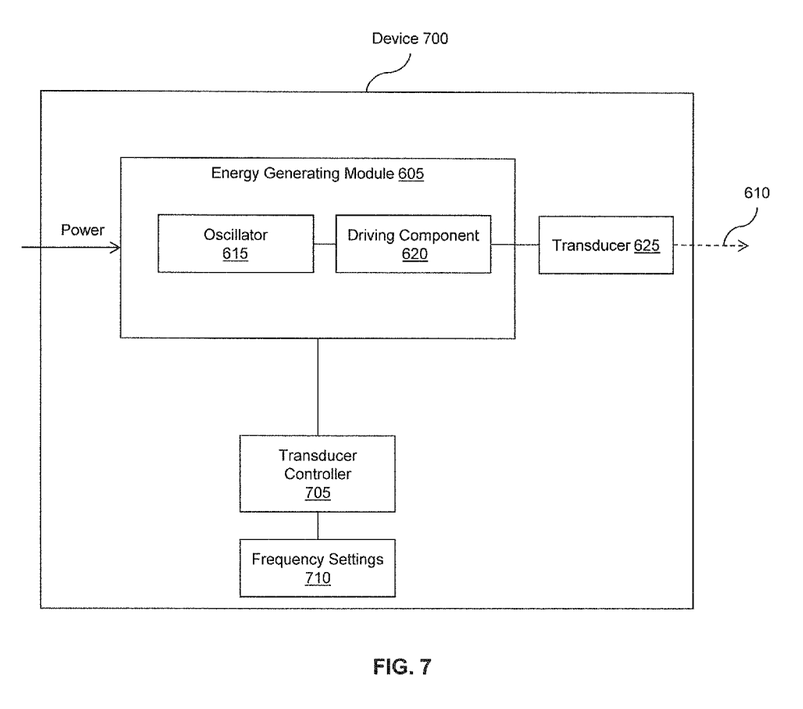
FIG. 7 illustrates one embodiment of a block diagram of an ultrasound device with a transducer controller that changes frequencies.

Thus, in one embodiment, the mobile ultrasound device 100 or 500 (see FIG. 1 or 5, respectively) is configured to automatically change ultrasound frequencies at periodic intervals. With reference to FIG. 7, one embodiment an ultrasound device 700 is shown in block diagram form, which is a based on the ultrasound device 600 of FIG. 6. In FIG. 7, the device 700 includes a transducer controller 705 that controls the transducer 625 of a manually-operated ultrasound device to perform an alternating sweep of different frequencies based on a time period.

The transducer controller 705 is electrically connected to the transducer 625 via the energy generating module 605. For example, the transducer controller 705 can be a logic component that is part of the energy generating module 605 or can externally control the module 605 as a different component within the handheld device 700. In another embodiment, the transducer controller 705 is implemented as logic within a host computer that sends control signals to the device 700 so that desired frequencies are generated at different times.

In one embodiment, the transducer controller 705 is a programmable logic configured to control the transducer 625 to generate selected frequencies of ultrasound at selected time periods. For example, the transducer 625 can be controlled to automatically alternate between two or more different frequencies at predefined time intervals (e.g., alternate between 1 MHz and 3 MHz every 4 seconds). Of course, other frequencies can be used and the device can cycle between a set of predefined frequencies. In one embodiment, the transducer controller 705 is configured to cause the transducer 625 to operate at different frequencies by changing the voltage or current that is applied to the transducer 625 from a power source via the energy generating module 605.

In one embodiment, the device 700 includes frequency settings 710 that are predefined and/or programmable. The frequency settings 710 include parameters stored in a memory that indicate various frequencies and time periods for changing between selected frequencies during operation of the ultrasound device 700. Default parameters may be set for the device and/or parameters may be selected by a user via a user interface. The transducer controller 705 may be configured to read selected parameters from the frequency settings 710 and control the transducer 625 according to those parameters.

In one embodiment, the transducer controller 705 is configured with a memory that contains the pre-defined frequency settings 710. The pre-defined settings 710 may be programmable via a user interface. In one embodiment, transducer controller 705 is configured using firmware that executes an algorithm for changing the frequency of the transducer 625 between two or more selected frequencies. The frequency can be changed based on a designated trigger event (e.g., a selected time interval, detected motion of the ultrasound device moving a certain distance, and so on). If motion is the trigger event, then the frequency is changed when the ultrasound device is moved, for example, every 2-3 inches or if the device is not moved for a threshold time period (e.g., to avoid overexposing one location to the same ultrasound frequency).

As an example operation, consider a physical therapy application where the frequency settings are selected to alternate between 1 MHz and 3 MHz every 4 seconds. Upon initiating an ultrasound procedure, the transducer controller 705 is configured to activate the transducer 625 (via the energy generating module 605) to operate at a first frequency (e.g., around 1 MHz). Assuming that a clinician operating the hand-held device 700 is moving the device 700 across a patient's skin at some speed, the transducer controller 705 changes parameters after a time interval (e.g., 4 seconds) causing the transducer 625 to operate at a second frequency (e.g., around 3 MHz).

After the next time period, the process repeats by alternating between the 1 MHz and 3 MHz frequencies. As the ultrasound device 700 is moved along the skin (or back and forth along an area), the alternating frequencies offer a good compromise between sufficiently deep penetration and adequate heating of the treatment area using varying ultrasound frequencies and exposure levels.

In one embodiment, device 700 is used in combination with a preconfigured piece of conductive medium (e.g., gel 140; see FIG. 1 or 4A) that is infused with a medicine/drug. Thus, when device 700 automatically changes frequencies, the change helps to drive the medicine/drug from the conductive medium into the skin of the patient for absorption.

In another embodiment, the ultrasound device 700 is configured to provide a signal (e.g., audible, visual (light), or both) each time the frequency changes. In another embodiment, the ultrasound device 700 may include a display screen that displays the current operating frequency.

In general, the device 700 simplifies the ultrasound procedure by not requiring the clinician to stop and manually change settings (e.g., changing a setting in a host device) in order to change the frequency of the ultrasound. This also helps to reduce human error in applying incorrect settings for an ultrasound procedure.

The automatic frequency changes of the device 700 provide additional safety to a patient. For example, if the clinician does not move the device 700 fast enough or maintains the device 700 in one location for too long of a time period, the device 700 is configured to change frequencies every few seconds. Thus, this reduces the risk of burning or damaging the skin caused by overexposure to the same ultrasound frequency at the same location during the therapy procedure.

Diaphragm With Protrusion Embodiment

Figure 8A:
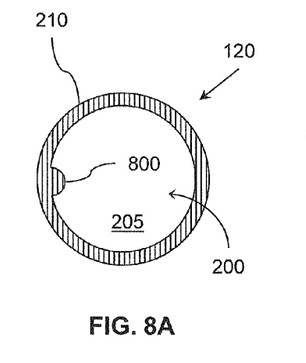
FIG. 8A illustrates a cross-section top view of another embodiment of the diaphragm including a protrusion.

With reference to FIG. 8A, another embodiment of the diaphragm 120 is shown that includes an interior protrusion 800. FIG. 8A is a top view of the diaphragm 120 similar to FIG. 2A that shows the sidewall 210 and cavity 200. The sidewall 210 is shown in cross-section. In FIG. 8A, the inner surface of the sidewall 210 includes one or more protrusions 800 that project out from the sidewall 210 and toward the cavity 200. For example, the protrusion 800 is a rib or other projection that may be configured in a desired shape and orientation. The protrusion 800 may extend vertically or horizontally along the sidewall 210 and there may be multiple protrusions 800 distributed along the inner wall.

Figure 8B:
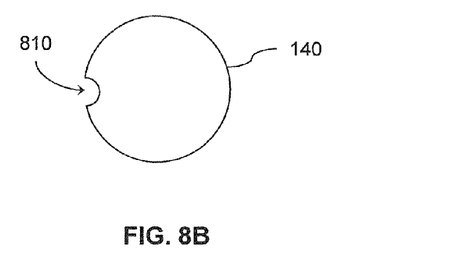
FIG. 8B illustrates another embodiment of the preconfigured medium including a notch to correspond with the protrusion of the diaphragm in FIG. 8A.

In one embodiment, the protrusion 800 is configured to assist in locking or otherwise holding a preconfigured gel 140 in place in the gel receiving cavity 200. For example, FIG. 8B illustrates another embodiment of the preconfigured gel 140 that includes a notch 810. The notch 810 is configured with a shape that corresponds to the protrusion 800 for connection therebetween. In one example, the notch 810 is a female counterpart of the protrusion 800.

Figure 8C:
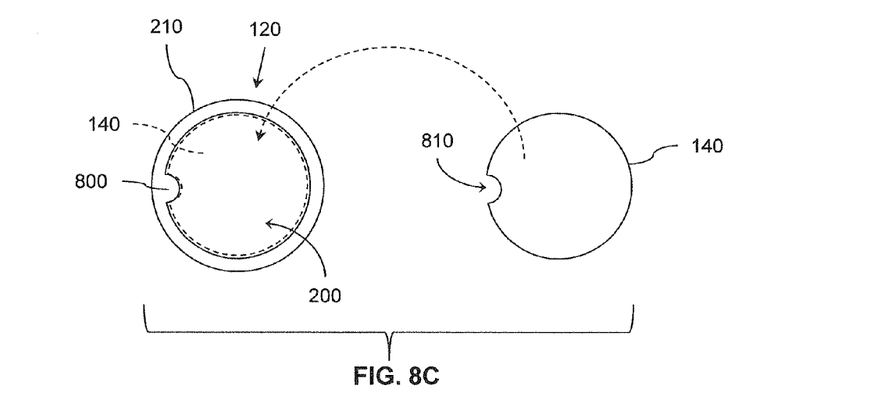
FIG. 8C illustrates the preconfigured medium from FIG. 8B inserted into the diaphragm of FIG. 8A.

FIG. 8C illustrates the preconfigured gel 140 being aligned and inserted into the receiving cavity 200. The gel 140 is shown as a dashed outline as it sits in the receiving cavity 200. With protrusion 800 inserted into notch 810 of the gel 140, movement of the gel 140 is restricted to ensure that the gel 140 does not inadvertently fall out during an ultrasound procedure.

In other embodiment, the protrusion 800 and notch 810 may have geometries and/or shapes other than the circular shape shown in FIGS. 8A and 8B, respectively. In other embodiments, both the sidewall 210 and the preconfigured gel 140 may have protrusions that are configured to interlock with each other (e.g., one protrusion fits on top of or under the other protrusion). For example, the sidewall 210 may have one or more lips, edges, or rings that project outward and are positioned to engage a corresponding lip, edge, or ring on the preconfigured gel 140.

Figure 9A:
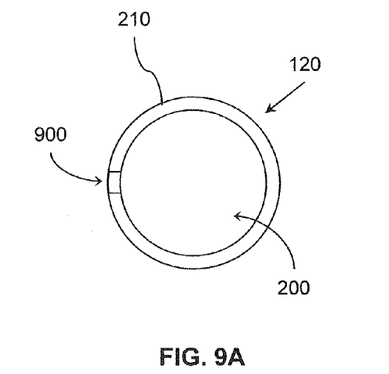
FIGS. 9A and 9B illustrate another embodiment of the diaphragm including a notch and the preconfigured gel with a protrusion, respectively.
Figure 9B:
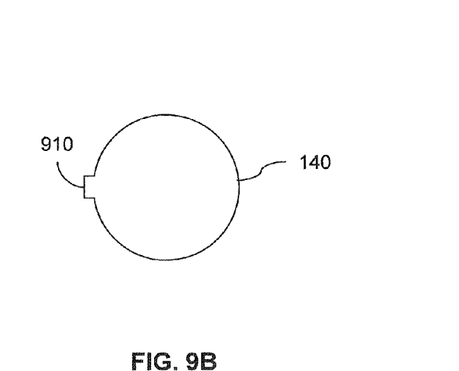

With reference to FIGS. 9A and 9B, a reversed embodiment of FIGS. 8A and 8B is shown where the diaphragm 120 is configured with a notch 900 in the sidewall 210 and the preconfigured gel 140 is configured with a protrusion 910 extending out from the preconfigured gel 140. Thus when the gel 140 is inserted into the receiving cavity 200, the protrusion 910 of the gel is aligned and inserted into the notch 900. Of course, other shapes and geometries may be implemented.

DEFINITIONS

The following includes definitions of selected terms employed herein. The definitions include various examples and/or forms of components that fall within the scope of a term and that may be used for implementation. The examples are not intended to be limiting. Both singular and plural forms of terms may be within the definitions.

The term "conductive medium" is used to refer to a substance that is used during an ultrasound procedure that assists in coupling the ultrasound device/probe head or applicator tip to a subject (e.g., the skin of a patient or other surface) and conducts ultrasound energy. Typically, the conductive medium is ultrasound gel but other substances can be used such as shampoo, hairstyling gel, hand lotion, hand sanitizer, liquid dishwashing detergent, olive oil (or other oil based substances), or other substance that is appropriate to function with an ultrasound device. These substances may be preconfigured into a semi-solid or solid form and used with the receiving cavity 200. References to the term "gel" is intended to refer to any of these conductive media that is appropriate for an ultrasound procedure.

References to "one embodiment", "an embodiment", "one example", "an example", and so on, indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

While example systems, methods, and so on have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and so on described herein. Therefore, the disclosure is not limited to the specific details, the representative apparatus, and illustrative examples shown and described. Thus, this disclosure is intended to embrace alterations, modifications, and variations that fall within the scope of the appended claims. All systems, methods, and devices of the claims are limited to statutory subject matter under 35 U.S.C. §101.

"Logic", as used herein, includes computer or electrical hardware, firmware, a non-transitory electronic medium that stores instructions/data, and/or any combinations of these to perform a function(s) or an action(s), and/or to cause a function or action from another logic, method, and/or system. Logic may include a microprocessor configured to execute an algorithm, a discrete logic (e.g., ASIC), an analog circuit, a digital circuit, a programmed logic device, a memory device containing instructions, and so on. Logic may include at least one circuit, one or more gates, combinations of gates, or other circuit components. Where multiple logical logics are described, it may be possible to incorporate the multiple logical logics into one physical logic. Similarly, where a single logical logic is described, it may be possible to distribute that single logic between multiple logics. Logic can be used to implement one or more of the components described herein or their equivalents. Logic is limited to statutory subject matter under 35 U.S.C. §101.

To the extent that the term "includes" or "including" is employed in the detailed description or the claims, it is intended to be inclusive in a manner similar to the term "comprising" as that term is interpreted when employed as a transitional word in a claim.

To the extent that the term "or" is used in the detailed description or claims (e.g., A or B) it is intended to mean "A or B or both". When the applicants intend to indicate "only A or B but not both" then the phrase "only A or B but not both" will be used. Thus, use of the term "or" herein is the inclusive, and not the exclusive use. See, Bryan A. Garner, A Dictionary of Modern Legal Usage 624 (2d. Ed. 1995).

What is claimed is:

1. A diaphragm for an ultrasound device comprising:
   a housing configured with a receiving cavity defined by one or more sidewalls, wherein the receiving cavity is configured to hold a preconfigured conductive medium; and
   a connector formed in the housing for connecting the diaphragm to a distal end of an ultrasound device, wherein the one or more sidewalls of the housing are within a perimeter of the distal end of the ultrasound device and define the receiving cavity to be within the perimeter of the distal end;
   wherein the sidewall of the receiving cavity includes (i) one or more protrusions that extend out from the sidewall, or (ii) one or more notches that are formed in the sidewall;
   wherein the preconfigured conductive medium is a solidified substance that is preconfigured into a solid form prior to being positioned in the receiving cavity; and
   wherein the protrusion or the notch is engaged with the preconfigured conductive medium to restrict movement of the preconfigured conductive medium after the preconfigured conductive medium is inserted into the receiving cavity.

2. The diaphragm of claim 1, further comprising an ultrasound transducer attached within the housing and being adjacent to the receiving cavity such that ultrasound energy generated by the ultrasound transducer is directed through the receiving cavity.

3. The diaphragm of claim 1, wherein the connector is configured to attach to and detach from the ultrasound device.

4. The diaphragm of claim 3, wherein the diaphragm is configured to retrofit on the ultrasound device wherein the diaphragm is attachable to a the distal end of an existing configuration of the ultrasound device to convert the distal end that does not include the receiving cavity to a configuration that includes the receiving cavity to hold the preconfigured conductive medium.

5. The diaphragm of claim 1, wherein the receiving cavity is a receptacle configured to allow the preconfigured conductive medium to be inserted into the receiving cavity in the solid form and removed from the receiving cavity.

6. The diaphragm of claim 1, wherein the preconfigured conductive medium is configured (i) with one or more notches that correspond to the one or more protrusions that extend out from the sidewall of the diaphragm, or (ii) with one or more protrusions that extend out from the conductive medium that correspond to the one or more notches in the sidewall of the diaphragm.

7. The diaphragm of claim 1, wherein the one or more protrusions or the one or more notches of the sidewall, or both, are formed as part of the sidewall and interlock with the preconfigured conductive medium and are configured to allow the preconfigured conductive medium to be lifted out of the receiving cavity and allow another preconfigured conductive medium to be inserted into the receptacle.

8. The diaphragm of claim 1, wherein the diaphragm is a retrofit head assembly wherein the connector is configured to attach to and detach from an existing head assembly of the ultrasound device, wherein the retrofit head assembly converts the existing head assembly that does not include a receiving cavity for holding the preconfigured conductive medium to a head assembly that includes the receiving cavity.

9. The diaphragm of claim 1, wherein the solidified substance of the preconfigured conductive medium comprises a medicine.

10. A head assembly for an ultrasound device, the head assembly comprising:
   a housing configured with a diaphragm wall disposed within the housing;
   a sidewall formed around a perimeter of the diaphragm wall and extending out from the diaphragm wall to define a first cavity, wherein the first cavity is configured to receive a portion of a conductive medium that is to be inserted into the first cavity, wherein the conductive medium is preconfigured in a solid form prior to insertion into the first cavity;
   wherein the sidewall includes means for interlocking with the preconfigured conductive medium that interlocks after the preconfigured conductive medium is inserted into the first cavity;
   a second cavity in the housing for containing an ultrasound transducer for generating ultrasound energy, wherein the ultrasound transducer is connected to an internal surface of the diaphragm wall, wherein the diaphragm wall is disposed between the first cavity and the second cavity in the housing; and
   a connector formed in the housing for connecting the housing to a distal end of an ultrasound device;
   wherein the first cavity is defined by the sidewall of the head assembly to be within a perimeter of the distal end of the ultrasound device.

11. The head assembly of claim 10, the conductive medium is a piece of preconfigured gel that is in a solidified state prior to insertion in the first cavity, wherein the sidewall and the first cavity are configured to hold the piece of preconfigured gel within the first cavity by the means for interlocking and maintain a position of the preconfigured gel relative to the ultrasound transducer within the ultrasound device during movement of the ultrasound device.

12. The head assembly of claim 10, wherein the first cavity is configured to hold the solid form of the preconfigured conductive medium wherein the means for interlocking comprises one or more protrusions that extend from the sidewall to engage corresponding protrusions or notches formed on the preconfigured conductive medium.

13. The head assembly of claim 10, wherein the connector is configured to be attachable to and detachable from the ultrasound device.

14. The head assembly of claim 10, wherein the head assembly is connected to the ultrasound device, and wherein the ultrasound device includes a transducer controller configured to cause the ultrasound transducer to generate ultrasound energy at different frequencies at periodic intervals.

15. The head assembly of claim 14, wherein the different frequencies include at least two alternating frequencies selected from predefined settings.

16. An ultrasound device comprising:
   a housing configured with a proximal end and a distal end, wherein the proximal end forms a handle portion;
   wherein the distal end comprises a receptacle configured to hold a preconfigured portion of conductive medium, wherein the preconfigured portion of conductive medium is preconfigured into a solid form prior to being inserted into the receptacle,
   wherein the receptacle is defined within a perimeter of the housing at the distal end by one or more sidewalls extending from the distal end,
   wherein the one or more sidewalls includes one or more protrusions configured to lock the preconfigured portion of conductive medium within the receptacle after the preconfigured portion of conductive medium is inserted into the receptacle; and
   a transducer connected within the distal end of the housing and configured to generate ultrasound energy to be transmitted through the receptacle.

17. The ultrasound device of claim 16, further comprising an energy generating module configured to generate a driving signal for controlling the transducer to generate the ultrasound energy.

18. The ultrasound device of claim 16, wherein the one or more sidewalls that define the receptacle are integrated with the distal end of the housing.

19. The ultrasound device of claim 16, wherein the one or more sidewalls that define the receptacle are connected to the distal end of the housing, and are attachable and detachable from the housing.

20. The ultrasound device of claim 16, wherein the ultrasound device is configured to automatically change ultrasound frequencies at periodic intervals.

21. The ultrasound device of claim 16, further comprising a transducer controller configured to control the transducer to perform an alternating sweep of different ultrasound frequencies based on a time period.

22. The ultrasound device of claim 16, wherein the one or more protrusions of the one or more sidewalls comprises a lip, an edge, or a ring that projects outward from the one or more sidewalls toward the receptacle.

* * * * *